United States Patent
Swenholt

(10) Patent No.: US 9,320,921 B2
(45) Date of Patent: Apr. 26, 2016

(54) NAIL FUNGUS TREATMENT AND COMPOSITION

(76) Inventor: Karen C. Swenholt, Mclean, VA (US)

(*) Notice: Subject to any disclaimer, the term of this patent is extended or adjusted under 35 U.S.C. 154(b) by 596 days.

(21) Appl. No.: 12/587,495

(22) Filed: Oct. 7, 2009

(65) Prior Publication Data

US 2010/0159031 A1 Jun. 24, 2010

Related U.S. Application Data

(63) Continuation-in-part of application No. 12/387,119, filed on Apr. 28, 2009, now abandoned.

(60) Provisional application No. 61/203,375, filed on Dec. 22, 2008, provisional application No. 61/207,268, filed on Feb. 10, 2009.

(51) Int. Cl.

| | | |
|---|---|---|
| A61Q 3/00 | (2006.01) | |
| A61K 33/14 | (2006.01) | |
| A61K 8/19 | (2006.01) | |
| A61K 8/365 | (2006.01) | |
| A61K 8/38 | (2006.01) | |
| A61K 31/235 | (2006.01) | |
| A61K 33/40 | (2006.01) | |
| A61Q 17/00 | (2006.01) | |

(52) U.S. Cl.
CPC ... A61Q 3/00 (2013.01); A61K 8/19 (2013.01); A61K 8/365 (2013.01); A61K 8/38 (2013.01); A61K 31/235 (2013.01); A61K 33/40 (2013.01); A61Q 17/005 (2013.01); A61K 2800/242 (2013.01); A61K 2800/884 (2013.01)

(58) Field of Classification Search
CPC . A61K 2800/884; A61K 8/365; A61K 33/14; A61K 8/19; A61K 33/40; A61K 8/20; A61Q 17/005; A61Q 3/00
USPC .......................................... 424/661
See application file for complete search history.

(56) References Cited

U.S. PATENT DOCUMENTS

| | | | | |
|---|---|---|---|---|
| 4,923,900 | A * | 5/1990 | De Villez | 514/714 |
| 4,986,990 | A * | 1/1991 | Davidson et al. | 424/665 |
| 6,132,702 | A | 10/2000 | Witt et al. | |
| 6,159,977 | A * | 12/2000 | Reeves | 514/254.07 |
| 2003/0224064 | A1* | 12/2003 | Kling | 424/661 |
| 2004/0106663 | A1* | 6/2004 | Talley et al. | 514/378 |
| 2005/0142215 | A1 | 6/2005 | Kling | |
| 2009/0092576 | A1 | 4/2009 | Trimble | |
| 2010/0074970 | A1* | 3/2010 | Ratcliff et al. | 424/661 |
| 2010/0084604 | A1* | 4/2010 | Abe | 252/182.33 |

FOREIGN PATENT DOCUMENTS

| | | |
|---|---|---|
| WO | WO 2006088790 A2 * | 8/2006 |
| WO | WO 2007113830 A2 * | 10/2007 |

* cited by examiner

*Primary Examiner* — Abigail Fisher
*Assistant Examiner* — Daniel L Branson
(74) *Attorney, Agent, or Firm* — Richards Patent Law P.C.

(57) ABSTRACT

Compositions and methods for treating or preventing fungal infections of the nail are provided. The topical composition includes the use of chlorine dioxide, chlorite salts, benzoyl peroxide, an alpha hydroxy acid, antifungal and antibiotic agents. Also provided is a heat-generating device for use in treating at least one nail infected with fungus and a toe sock device.

15 Claims, 6 Drawing Sheets

NAIL FUNGUS TREATMENT AND COMPOSITION

This application claims the benefit of my earlier filed provisional applications, Ser. No. 61/203,375, filed on Dec. 22, 2008, entitled Nail Fungus Treatment, Ser. No. 61/207,268, filed Feb. 10, 2009, entitled Nail Fungus Treatment, and provisional application filed Aug. 15, 2009 entitled Deep Nail Cleaning Whitening and Brightening Agent, and is a continuation-in-part of patent application Ser. No. 12/387,119, filed Apr. 28, 2009 entitled Nail Fungus Treatment.

TECHNICAL FIELD AND INDUSTRIAL APPLICABILITY OF THE INVENTION

The present invention relates generally to methods and compositions for the treatment of dermatological conditions in humans and, more particularly, to methods of treating fungal infections of the nails. Devices for use in such methods are also provided.

BACKGROUND OF THE INVENTION

About 7% of Americans suffer from onychomycosis, a fungal infection of the nail, particularly the toenail. More than 90 percent of cases are caused by one of two pathogens: *Trichophyton rubrum* or *Trichophyton mentagrophytes*. Factors that have an important effect on the development of onychomycosis include increasing age; genetic susceptibility; and the presence of certain disease states such as diabetes, acquired immunodeficiency syndrome, or peripheral arterial disease. Of particular concern are diabetics who are nearly three times more likely to develop onychomycosis than non-diabetics. It has been reported that up to one third of diabetics develop nail fungus. In diabetics, slow healing, particularly in the feet, is common and foot infections of all types can be difficult to treat and may end in amputation.

Feet exposed to a warm, dark, moist environment can get infected. Some people may already be genetically predisposed to onychomycosis. For those who are susceptible, the condition is highly contagious. The best way to avoid onychomycosis is to keep feet clean and dry, washing them at least once a day and drying the toes well. Shoes and socks should be changed daily and should also be kept dry.

Onychomycosis is a medical condition with cosmetic impact because it disfigures the nails. Nails can become thick, discolored, loose, brittle, hard, yellow and painful. Nails are epithelial structures derived from primitive epidermis made up of keratinous fibrils. Once nails are infected, even if healthy nail is grown out, the susceptibility to infection may remain and the condition can relapse. Furthermore, healthy nails can be reinfected.

There appears to be no certain cure for onychomycosis. Current treatments include medications such as itraconazole, terbinafine, ciclopirox and fluconazole, respectively sold under the names Sporonox®, Lamisil® and Diflucan®. Unfortunately, such medications do not eradicate the problem for many patients. Instead, such treatments typically take months to work, depend on the nail bed growing out completely, and are sometimes damaging to the liver. Moreover, through the course of treatment patients oftentimes re-infect themselves. Indeed, only about 12% of patients treated with Sporonox have fungus-free nails after one year. Infected nails may also be debrided (cut and thinned) with uncertain results. As a last resort, infected nails may be surgically removed.

U.S. Patent Application Number 20080207537 includes chlorine dioxide in a long list as a non-preferred oxidizing agents for increasing permeability in the treatment of onychomycosis. The patent application, however, requires a reducing agent followed by an oxidizing agent separately and sequentially.

Thus, there is an existing need in the art for a method of treating onychomycosis that is safe, quick, and effective.

SUMMARY OF THE INVENTION

It is an object of the present invention to provide a method of treating onychomycosis. The method of treating onychomycosis generally includes the application of chemical compositions to the nail and surrounding tissues. Applying heat to the infected nail may also be used alone or in combination to kills the fungus without damaging the nail surface.

The method of the present invention may also include the application of chlorine dioxide either in the active or stabilized formats and/or oxychlor compounds or complexes to the infected nail. Chlorine dioxide is a disinfectant. Chlorine dioxide is also listed by the National Department of Agriculture as an antifungal, with kill rates of 99.99999% for certain fungus and their spores. Chlorine dioxide containing compositions may be used alone as an anti-fungal that penetrates the nail bed.

The method of the present invention also includes the use of combinations of chlorine dioxide in solution with a chlorite salt. The chlorite salt may function to provide chlorine dioxide to the solution or to maintain a saturated concentration of chlorine dioxide. The combination may also include different types of compounds which when combined produce a more pronounced anti-fungal effect. Benzoyl peroxide is particularly preferred to be used in combination. Alpha hydroxy acids such as glycolic acid may also be used simultaneously for both their direct effects on fungi infected nails and also surrounding skin. Pealing agents such as salicylic acid and other organic acids (e.g. trichloroacetic acid), specific antifungal compounds such as Miconazole, Terbinafine and Tolnaflate, and broader spectrum antibiotics such as Bacitracin, Neomycin, and Polymyxin B may also be used simultaneously.

Another method of the present invention may further use chlorine dioxide containing compositions when combined with a fungistatic or, preferably, a fungicidal agent such as terbinafine. In this embodiment, the chlorine dioxide acts in conjunction with effective concentrations of an anti-fungal, such as but not limited to terbinafine.

It is another object of the present invention to provide devices for use in the methods of the present invention.

It is yet another object of the present invention to provide a method for maintaining the health of the nails throughout treatment of onychomycosis and after its eradication. Patients have been known to re-infect themselves with their shoes. The method generally includes heating shoes to temperatures above that which fungi that cause onychomycosis can live. The shoes may be heated using a shoe heater such as a shoe insert with a heating element or a specialized heating oven. It is likely that healing from other fungal infections of the foot such as tinea pedis can be maintained through use of this device. Alternatively a shoe insert that uses a light based system adopting Noveon technology could be used for this device.

The processes of the present invention may be used alone or in conjunction with one another not only as a method of treating onychomycosis, but also to control the symptoms of onychomycosis, to prevent onychomycosis, and to maintain the health of the nails after diminishing and controlling the symptoms of onychomycosis.

One advantage of the method of treating onychomycosis according to the present invention is that it creates a hostile environment for onychomycosis. The hostile environment means that the onychomycosis can no longer grow unchecked and thrive in the nails. Sufferers of onychomycosis typically have heavily damaged nails, which contribute to maintaining an environment for the growth of fungus. Upon successful treatment, nails also lose characteristics that create a positive ecosystem for onychomycosis. The now-compromised fungus may be easily removed with tweezers or similar tools.

Another advantage of the present invention is that it is safer than current medications in that it does not harm the user's liver.

Yet another advantage of the present invention is that the preferred formulation of active chlorine dioxide does not irritate either the nail or the skin surrounding the nail when used at pharmacologically effective concentrations.

Yet another advantage of the method of treating onychomycosis according to the present invention is that it creates dramatic results as early as after one day to one month of treatments, where such results do not depend on the nail growing out.

Yet another advantage of the present invention is that the method penetrates under the nail, where other topical treatments cannot, thereby effectively eroding the fungus located under the nail.

Yet another advantage of the present invention is that chlorine dioxide containing compositions act in conjunction with fungistatics or fungicides such as, but not limited to, terbinafine. Chlorine dioxide containing compositions are known to eliminate biofilms, which are layers of microorganisms contained in a matrix that forms on surfaces and may be in contact with water. Pathogens in biofilms can protect the pathogens from biocides that would kill organisms freely suspended in water. The biofilm defense parallels the fungal mat that topical antifungals alone do not penetrate well. Certain components of the compositions of the present invention may diffuse through the nail alone or when used in conjunction with other components that function as penetration enhancers.

Yet another advantage of this invention is that hard brittle nails soften to a more normal consistency through the use of this invention. The nail is thinned to a natural appearance as the fungus and the environment of the fungus are impacted.

The foregoing and other objects and features of the invention will appear more fully hereinafter from a consideration of the detailed description that follows.

DETAILED DESCRIPTION AND PREFERRED EMBODIMENTS OF THE INVENTION

Figure 1:
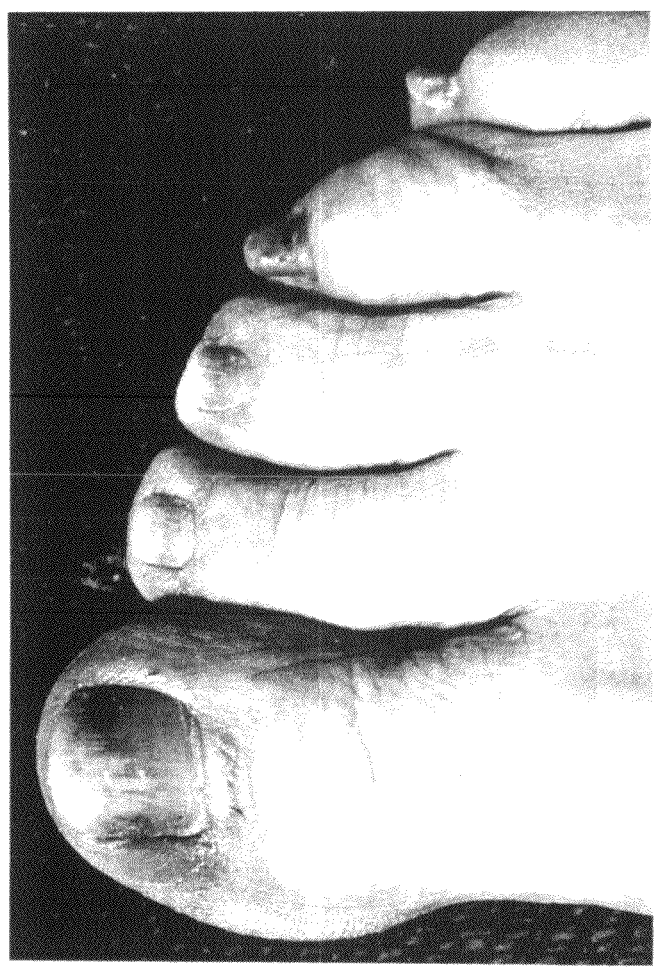
FIG. 1 is a photograph of the infected toenails of subject A before treatment.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are described herein. All references cited herein, including published or corresponding U.S. or foreign patent applications, issued U.S. or foreign patents, and any other references, are each incorporated by reference in their entireties, including all data, tables, figures, and text presented in the cited references.

While not being limited to any particular theory, it is speculated that chlorine dioxide and other compounds may act a penetration enhancers in addition to any other anti-fungal activity. Likewise, certain components may act as pealing agents to remove dead or diseased tissue. Additionally, certain components may act additively or synergistically with each other or by different mechanisms to provide a desired combined effect.

General observations suggest certain functions, and while applicant does not wish to be bound to any theory, the following is noted. While all components have their usual and expected properties of killing fungi and other functions, many have a second and/or new function. The chlorite salts in high concentrations, over about 1%, alone and/or (as a generating component of) chlorine dioxide, appears to enhance penetration of other components through the nail. The benzoyl peroxide appears particularly beneficial at preventing relapse. Antifungal agents function with broad-antibiotics even when the antibiotic is primarily an antibacterial agent. Alpha hydroxy acids and salicylic acid seem to function as penetration enhancers across the nail. It is these combined or new effects, which makes the present invention superior to existing treatments.

The preferred daily use of the present invention penetrates but does not damage healthy tissue as alpha and beta hydroxy and other organic acids can. The present invention can make use of such potentially beneficial properties without unacceptable damage by using lower concentrations, using them in combination with other compounds and/or using them in a protocol which uses them discontinuously while maintaining daily treatment with antifungal, penetration and other agents.

While all discussion below relates to the prevention and treatment of humans, the invention equally applies to veterinary uses for livestock, wild and companion animals for fungal infections of nails, claws, hooves, horns and antlers.

Due to the long-term nature of the fungal infection, biofilms may form which are difficult to treat and chemical agents acting on the biofilm without actually killing the fungus may also be considered to be anti-fungal. Under the nail, the fungus may be considered matted in portions rather than a biofilm. Nonetheless, anything that somewhat specifically degrades the structure or causes the fungal cells to be harmed is considered a suitable antifungal agent.

The present invention relates to methods and compositions for topically treating fungal infections on the surfaces of the body. These compositions may be used on skin, hair, wounds and the like for the purposes of inhibiting and treating microbial infections. More preferably, the compositions of the present invention may be used for treating fungal infections, particularly those of the nails including onychomycosis.

Compositions used in the present invention include those in one container and those prepared from multiple containers. The nature of some of the chemicals used makes them react with each other over time resulting in a product, which lacks one-year (or greater) shelf stability. In such a situation, the present invention may be a kit containing two or more containers of chemicals such that chemicals reactive with each other are kept in separate containers. Compounds that are stable together are preferably premixed. The contents of the containers may be mixed immediately prior to use, added simultaneously or sequentially at the target site of infection or may be mixed together ahead of time and briefly stored before use. For example, some components may be mixed in liquid form and stored for example, about two months or so whereas the original components may be shelf stable for over one year. Storage under refrigeration or freezing conditions may extend the acceptable storage time. The final kit may include packaging for the two or more containers and instructions for preparation and use. Individual containers may contain any form of solids, liquids, gels, ointments, creams, etc. At least one of the containers or an additional empty container may be resealable after dispensing its contents after each application.

More specifically, one may use a two (or more) barrel syringe or other multichambered container to co-extrude the different composition components which are either mixed immediately before applying to the nail or are applied simultaneously or sequentially on the nail.

An alternative container may be a multipack containing individual dosages of one or more of the containers. For example a bottle containing capsules (or other individual dose container) where each capsule contains one or more components of the composition of the present invention. Different bottles may contain different capsules and different capsules may be opened immediately before use.

The components may also be held in the form of an emulsion with the active ingredients in one or more discontinuous phases in the emulsion. Water-in-oil emulsions are particularly preferred. This allows reactive components to be kept apart until mixed and applied. Furthermore, judicious selection of the continuous phase may entrap volatile or reactive compounds away from each other leading to a longer shelf life.

The present invention also relates to methods of preventing and treating fungal infections of the nails. In one embodiment, the method of treating fungal infections of the nails according to the present invention includes the use of heat to kill the fungus. Any heat that penetrates the infected nail without damaging or burning the nail surface until the fungi has been damaged or destroyed may be used. Preferably, the heat is infrared heat. This includes both directly applied infrared heat and diffused radiant infrared heat. Far red infrared heat can penetrate about one and one half inches into skin and is a preferred but non-limiting embodiment of this invention.

It is believed that the heat not only kills fungus, but also opens up the fortress wall of keratin tissue on the edge of the infected nail, which seals in an ideal environment suitable for fungi. It is further believed that this hard-edged seal keeps topical medicines from working because such topical medications cannot penetrate past the seal to the nail bed where the infection actually lies. Heavily infected toes are piled high with fungus-laden keratin debris that prevents topical medications such as, for example, those sold under the names of terbinafine, Reclear®, Fungicure® and Mycocide®, from reaching all the infected tissue.

According to this method, the heat is applied to the infected nail using a heat-generating device. An exemplary heat-generating device for use in accordance with the present invention has a heating element, or blade mounted on a non-heat-conducting casing for holding the heat-generating device in the user's hand.

As previously noted, the heat-generating device used in accordance with the present invention generally includes a heating element (or blade). The heating element may be flat, convex or curved. The heating element may be spatula shaped or rounded. Alternatively, the heating element may be shaped in such a way so that it conforms to the shape of the specific finger or toenail being treated. Preferably, the heating element is narrow in depth so as to permit precise heating of the nail edge and under the nail. In particular, the size of the heating element is from about ¼ inch to about ½ inch wide. Interchangeable blades would allow the user to more precisely match the blade to the individual nails being treated. The blade can be rigid or somewhat flexible.

The heating element or blade may be any material that supplies heat to the infected nail with the object of killing nail or foot fungus by heating the nail without damaging the surface of the nail. The preferred material for the heating element is ceramic. Non-limiting examples of suitable heating elements are those commonly referred to as "ceramic plate" and "tourmaline ceramic plate." Other ceramic plate compounds such as silver may also be used. The heating element may be surrounded by a thin edging of non-conducting plastic to protect the cuticle and skin around the nail from being injured by heat. In a particularly preferred embodiment, the heat-generating device includes a small, blunt blade of far infrared radiant heat-producing ceramic plate that may be applied to the infected nail.

Other possible heat-generating devices may include, but are not limited to, ceramic heating plates designed to fit individual users by the molding and casting process. Protection of surrounding tissue can be achieved with fabrics similar, but not limited, to thin flat cotton pads such as are used for cosmetic purposes. Thus, the heat-generating device may consist of heavier insulation surrounding five nail-sized plates exactly molded to the user's foot or hand that can be turned off and on with a radiometer to determine when the heat reaches the nail bed.

According to the present invention, the heat can be applied by placing the heating element of the heat-generating device directly to the infected nail. Though the nail is directly exposed to the heating element according to the present invention, the nail is not burned or hurt because of the character of the heat and the heating element, as well as the length of time of its application. For example, a cotton ball pressed upon the ceramic heating element will not be singed or appear damaged in any way, yet the interior of the cotton ball is heated. Additionally, when the nail is heavily impregnated with fungus there is no pain on initial application perhaps because the fungus acts as a heat barrier to the skin beneath the nail, thereby insulating the nail and the skin. An unpleasant hot sensation may be felt after the fungus has been affected, i.e., damaged or destroyed. In one embodiment, the heat-generating device may also include a radiometer (not shown) that sounds when the nail bed is reached. At such time, the device is lifted off the nail surface, which is not hurt, though the fungi adhering to the underside of the nail is damaged or killed.

The heat can also be applied by placing the heat-generating device on an object such as, but not limited to, a cotton shield, which simply rests on the infected nail. One non-limiting example of such a shield is a dry square of lightly layered soft gauze cotton marketed under such names as cosmetic wipes. Use of a shield between the heating element and the nails being treated generally allows for longer exposure of the fungi to the heat. With the cotton shield, more than sixty seconds of heat may be comfortably applied to heavily infected nails. In another embodiment, removable cotton shields that glove the heating element rather than just being placed on top of the nail being treated may be used. A sock with holes for toes would add another layer of insulation.

The temperature of the heat-generating device may be from about 35° C. to about 300° C., preferably from about 50° C. to about 250° C., and most preferably from about 160° C. to about 200° C. The heat may be applied to the infected nail for a period of time ranging from about 1 second to about 60 seconds, preferably from about 7 seconds to about 30 seconds. The length of time for application of heat may be determined by the depth of the fungus growth and its insulating properties with severely infected nails requiring longer periods of heat. When heat is felt, the treatment has penetrated to healthy tissue and the ceramic blade is removed. Heat applications may be repeated from about one to about three times per nail per treatment. Up to two treatments per day is preferred.

Both far red infrared heat and chlorine dioxide appear to stimulate and accelerate nail growth. Typically, infected toenails take from about 10 to about 14 months to grow out. The currently prescribed ingested medications are typically prescribed for only short, three-month courses of treatment or slightly longer irregular "bursts" of therapy because such treatment must be interrupted to monitor impact of the medications on the liver. Such medications, therefore, do not remain in the bloodstream throughout the time needed for complete nail growth, thereby resulting in relapses.

Because far red infrared heat and chlorine dioxide appear to speed nail growth, more of the nail grows out in a shorter time, potentially positively impacting recovery rates compared to those obtained from the use of oral medications. This makes the heat treatment of the present invention a suitable partner to currently prescribed ingested medications. Treatment in accordance with the present invention can be augmented by use of topical anti-fungal lotions and ingested medicines to prevent recurrence and continue the assault on the environment of the fungus. Using heat to treat nail fungus according to the present invention, along with ingested medications and/or topical medications dramatically improves results of such medications because the nails grow out while the anti-fungal medications remain in the nail bed.

Optionally, after 2-4 applications of heat in accordance with the present invention, a narrow, flat plastic device may be gently yet firmly inserted underneath the nail to separate the fungus from the underside of the nail. This is done most preferably while the nail is still warm from the application of the infrared heat, as the heat appears to soften the hard-edged keratin wall that is not otherwise easily penetrated. Additionally, a second probe may be made beneath the fungus to separate the fungus from the skin of the toe, which would be touching the nail were it not for the fungus.

In a second embodiment, the method of treating fungal infections of the nails according to the present invention includes the use of chlorine dioxide and/or oxychlor compounds, both in the stabilized or, active formats. The concentrations are preferably about 1 to about 60 ppm of chlorine dioxide, more preferably 20-40 ppm. Alternatively, the concentration of chlorine dioxide in liquid may be up to saturating concentrations, which depends upon the temperature. Saturating conditions may be maintained by having a chemical generating system so that additional chlorine dioxide is being synthesized constantly or in response to loss of chlorine dioxide by leakage, decay or use during treatment.

A preferred component of the present invention is the use of a chlorite salt. This component may function by generating chlorine dioxide under acidic conditions and/or maintaining saturated chlorine dioxide conditions. While the sodium salt was exemplified, other salts may be used such as potassium, calcium, magnesium and other salts. Concentrations in the range of about 1% to about 5% are preferred. Concentrations above 2% and below 3.5% are particularly preferred. It is preferred for the pH to be maintained such that a small amount of metal chlorite is converted into chlorine dioxide for use in the present invention. For example 0.66% chlorite generates to a suitable chlorine dioxide concentration. For compositions where one wishes a 1% chlorite in chlorine dioxide composition, one may add 1.66% metal chlorite along with an acid or other suitable reagent to degrade some of the metal chlorite into chlorine dioxide.

Benzoyl peroxide and similar compounds is also a preferred component of the present invention. The preferred form is finely milled pharmaceutical grade. Concentrations in the range of 1% to 20% are preferred. 6-10% are more preferred particularly when used in conjunction with 1-3% metal chlorite and an antifungal and antibiotic.

Alpha hydroxy acids are well known for use in the skin treatment and are a preferred component of the present invention. Representative alpha hydroxy acids include mandelic acid, lactic acid, glycolic acid, etc. and salts thereof. One or more of these (or their salts) may also be used to serve as a pH adjusting agent or a buffering agent. While citric acid/citrate buffer is typically used, other pH-adjusting agents or buffering agents may be used alone or in combination with the alpha hydroxy acids of the present invention. Concentrations in the range of about 0.1% to about 20% are preferred. Depending upon the specific compound used and/or the intended frequency of use, narrower ranges are preferred. More preferred are ranges such as 0.2%-2% glycolic acid for daily use.

Salicylic acid may also be used in the present invention. Concentrations in the range of 0.2 to 20% may be used, preferably 0.5 to 8%, more preferably 1 to 5%. Other organic acids may be used, especially those which are known pealing agents such as trichloroacetic acid.

A specific antifungal agent is also a preferred component used in the present invention. While many compounds will destroy fungi non-specifically, such as concentrated sulfuric acid, for the purposes of this patent, a specific antifungal agent is one that has previously been recognized as a treatment for fungal infection. It may be applied topically or administered systemically.

A broad-spectrum antibiotic or combination of antibiotics may be administered topically or administered systemically. In the experiments below, Neosporin was used because of its long history of topical usage. Other topical or systemic antibiotics may be used that are active at inhibiting bacteria in the nail bed and surrounding areas. While antifungal agents may be included in the category of antibiotics, in the present invention these antibiotics may be better described as broad-spectrum anti-bacterial agents also. While fungi are the primary infecting agent in onychomycosis, considerable dead and damaged tissue are produced during the infection which provides suitable conditions for growth of other microorganisms which may metabolize or otherwise reduce the effectiveness of antifungal treatments.

The method of the present invention may also include the use of one or more of the protease inhibitors, which may be applied to the infected nail. Representative protease inhibitors include cystatin A, cystatin B, cystatin C, cystatin S, and cystatin SU.

Other optional ingredients include the use of diluents, salts to make the compositions isotonic, emollients, humectants, pH buffers, beta hydroxy acids, thickeners, stabilizers, abrasives, anti-inflammatory agents and chemicals involved in generating chlorine dioxide such as a metal salt of hypochlorite.

The final form of one or more components to the composition of the present invention is preferably liquid or spreadable solid (paste, gels, powders, ointments, etc.). A soap product containing some of the components of the composition of the present invention may be formed. This soap may be either in liquid or solid bar form. Components that are incompatible or volatile may be provided separately such as in a dropper bottle. In such a way a person may wash and simultaneously treat infected nails or prophylacticly apply some or all of the components to the nails, and if necessary followed by application of one or fewer liquids to the nails. Optionally, one may formulate a treatment bar with a different solidifying agent that resembles a soap bar but without the active soap ingredient. One example would be with the use of stearyl alcohol as the solidifying agent.

In an embodiment, chlorine dioxide and/or oxychlor compounds may be applied directly to the infected nails, nail bed and surrounding skin. The chloride dioxide and/or oxychlor compound may be applied to the nail in any form, but it is preferred that the compound is in solution or emulsion form. Any chlorine dioxide or oxychlor compound that negatively affects the presence of onychomycosis in the finger and toenails may be used in the present invention.

Non-limiting examples are "Oxy-chlor" or stabilized chlorine dioxide composition marketed under such names as AktivOxigen and Oxyd-8®. The expression "stabilized chlorine dioxide" as used in the art is actually a misnomer but reflects the attempt to control volatile chlorine dioxide/chlorine dioxide gas. One standard meaning of stabilized chlorine dioxide is an aqueous solution predominating in sodium chlorite ($NaClO_2$), with lesser amounts of sodium chlorate ($NaClO_3$), sodium chloride (NaCl) and at least one stabilizer to either retard degradation of sodium chlorite to chlorine dioxide or re-convert the chlorine dioxide degradation product back to sodium chlorite. According to the present invention, AktivOxigen and Oxyd-8® can be used diluted with water at a ratio variable from about 1 drop AktivOxigen:5 drops of water to about 2 drops of AktivOxigen:1 drop of water. The preferred ratio is empirically determined. In a preferred non-limiting example, AktivOxigen is used with chlorine dioxide and applied before and after a therapeutically effective dose of an anti-fungal drug.

One formulation of chlorine dioxide useful in the present invention is found in the product Pro-Fresh® which is available from ProFresh International Corporation, Philadelphia, Pa. According to U.S. Pat. No. 5,738,840, which is believed to contain the formulation of ProFresh for use in the oral cavity against bad breath, and is incorporated herein by reference in its entirety. When one uses such a formulation of chlorine dioxide in accordance with the present invention, no additional reducing agent is necessary. Active or molecular chlorine dioxide does not significantly irritate skin in the concentrations used.

Other methods for producing chlorine dioxide containing liquids may be used including reacting a chlorite salt with an acid.

A double strength concentration of the described formulation of chlorine dioxide for mouthwash (ProFresh) has been observed to be effective against onychomycosis. Higher concentrations up to about eight times the strength described may also be used. Typical concentrations would be 40 ppm chlorine dioxide.

In another embodiment where one or more protease inhibitors are applied to the nail either in combination with chlorine dioxide and/or other components together with or after about 1 to about 20 minutes, preferably about 10 minutes, after the application of chlorine dioxide.

In a third embodiment, the method of treating fungal infections of the nails according to the present invention includes the use of chlorine dioxide, as a penetration enhancer of the nail when used with existing fungicides. Without a reducing agent, chlorine dioxide is known to eliminate biofilms, which are similar in function to the fungal mats produced by the dermatophytes responsible for onychomycosis. Chlorine dioxide appears to increase the diffusion of existing topical treatments through the nail bed, perhaps by changing the nail structure. In Example 4 below this effect is believed to occur. Whether or not any of the agents described herein as penetration enhancers actually increase penetration, they appear to operate well in conjunction with other active compounds in the composition. For the purposes of this application, compositions that provide an added effect to other active ingredients when used in the intended use environment are sometimes referred to as penetration enhancers. Penetration enhancers as used herein are targeted and do not substantially harm the skin.

Suitable drugs for use in the formulation of the application of chlorine dioxide as a penetration enhancer according to the present invention include any and all specific antifungal drugs or compounds that are effective against onychomycosis. A non-limiting list includes amorolfine, amphotericin B, carbol-fuchsin, ciclopirox, clotrimazole, dapsone econazole, fluconazole, flucytosine, griseofulvin, Gentian Violet, haloprogin, itraconazole, ketoconazole, mafenide, miconazole, miconazolekl, naftifine, nystatin, oxiconazole, silver sulfadiazine, sulconazole terbinafine, tioconazole, tolnafiat, undecylenic acid, voriconazole, and pharmaceutically acceptable salts and esters thereof. Particularly preferred is terbinafine.

In this embodiment, chlorine dioxide may first be applied to the nail before the antifungal and then again after the antifungal is applied to the nail or in any combination. In the alternative, the antifungal medication may be present in a preparation containing another component. The protease inhibitors may or may not be added to the chlorine dioxide in this embodiment.

The applications of such compositions for periods of about an hour or more have a significant impact on the fungus. Other treatments were found effective after only 15 minutes. The frequency of applications and duration of each application will depend upon the individual being treatment and strength of the topically applied compositions. Individual components of the composition may be added in any order sequentially on the nail or premixed before application.

Reinfection and/or relapse are common occurrences in individuals having nail fungus. It is therefore an embodiment of the present invention to treat the individual prophylacticly. Prophylactic treatment may be performed periodically or after exposure to conditions that are known or suspected to potentially cause reinfection, relapse or heightened susceptibility to nail fungus. For example, after exposure to a public swimming pool, public shower, used towels, other infection, nail injury, immune suppressing event, other disease state or increased age.

After application of the chlorine dioxide compounds to the infected nails according to the above-described methods of the present invention, fungus impregnating the skin and under the nail appears to whiten like dying tissue. The altered softened fungus may then be removed by shallowly inserting a narrow, flat device underneath the nail and lifting out the compromised fungus or dead tissue. Care should be taken not to probe too deeply with the narrow, flat preferably plastic device. The narrow flat device may be used to gently remove compromised fungus from beneath the nails thereafter about every 2 to about every 12 days during treatment. Removal of some of the crumbling impacted fungus allows for better application of any further treatments. Alternatively, and preferably, a device used to trim cuticles with a narrow tip and pincer action can be used to pull compromised fungus out, sometimes completely.

In yet another embodiment of the present invention there is provided a toe sock or finger glove. The toe sock may be made of any suitable material, but preferably impermeable to the liquids being applied such as one made of rubber or latex. The purpose of the toe sock is to force or maintain the compositions of the present invention onto the infected nails and skin so that it does not dissipate into the atmosphere. The dermatophytes responsible for onychomycosis become deeply embedded in tissue surrounding the nails creating a roughened layered abnormal looking skin. The toe sock is also beneficial for clearing fungal impacted skin around the nails quickly.

Preferably, each toe is encased in the toe sock individually, like a glove on the hand. The sock can be worn for as long as necessary, preferably from about 30 minutes to 4 hours. The sock can be worn effectively for periods as short as about 10 minutes. Longer times may achieve superior effects. All day use of the toe sock inside shoes is also possible. The toe sock may be such that it is worn on the entire foot. The toe sock may also be such that it can be worn on individual toes. In use, a liquid of the present invention may be applied to the infected nails, and then the toe sock placed on the user's feet or individual nails. Alternatively, the composition(s) may be placed in the toe sock and then the toe sock applied to the user's feet or toes. Yet another way to use the toe sock is to apply the composition(s) to the toes by dropper after the toe sock is put on. In this situation, the toe sock will be permeable to the applied compositions. The toe sock may contain one or more pads to hold additional liquid treatments of the present invention against the infected nails. The toe sock permits long exposure to the selected compounds, thereby killing and inhibiting fungal reproduction for effective blocks of time. The finger glove or toe sock is preferably impermeable to chlorine dioxide gas and liquid components of the compositions of the present invention.

A penetration enhancer may be added prior to application of the compositions of the present invention optionally followed by applying the toe sock, a fungicide or fungistatic topical composition. Subsequent and/or repeated treatments may then be added again during the same treatment time.

The various embodiments of the present invention may be used alone or in conjunction with one another.

The methods of the present invention may be repeated up to 5 times a day (i.e., morning and evening and more as needed) for as long as necessary. Other treatment protocols may be used also. Lightly infected nails may be cleared in about 3 to about 7 treatments. Extremely infected nails will require more and treatment may be continued at least until the infected nails grow out. In such cases, good nail appearance can be achieved by the control of the presence of fungus until grow out clears the nail. It is anticipated that the methods of the present invention may be repeated for a period of about 2 days to about 12 months. After the fungus is reduced or eliminated, the treatments may be used occasionally as a preventative or renewed upon relapse. The specific route, dosage, and timing of administration will depend, in part upon the extent of the infection being treated and the individual.

Figure 2:
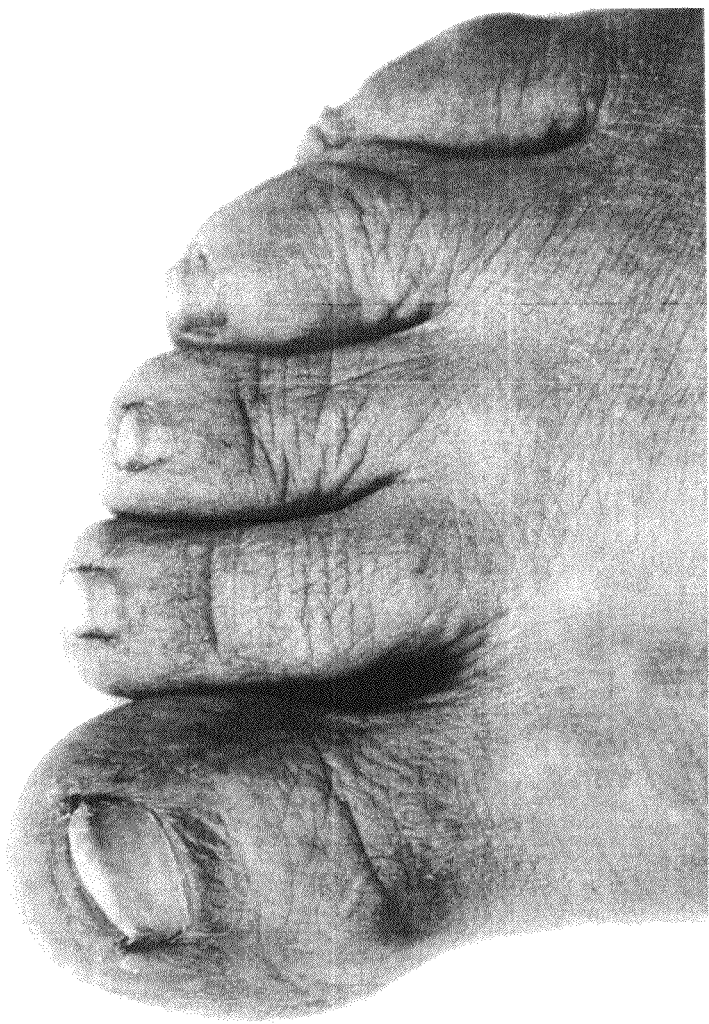
FIG. 2 is a photograph of the toenails of subject A after more than 30 days of treatment.
Figure 3:
FIG. 3 is a photograph of the infected toenails of subject B before treatment.
Figure 4:
FIG. 4 is a photograph of the toenails of subject B after 7 days of treatment.
Figure 5:
FIG. 5 is a photograph of the infected toenails of subject C before treatment.
Figure 6:
FIG. 6 is a photograph of the toenails of subject C after one day of treatment.

FIGS. 1-6 are photographs of treatments on three different individuals using three different treatment compositions and for three different treatment times. The success in all of these demonstrates the general applicability of the present invention. The treatment for FIG. 2 was composition 6G repeated no more than 4 times a week and enhanced and maintained by twice daily treatments of composition 1A or 6E. The treatment for FIG. 4 was composition 1A twice per day. The treatment for FIG. 6 was composition 6D for two treatments, one evening, one morning. The photo was taken 3 days later.

The present invention also includes a method for maintaining the health of the nails while eradicating the symptoms of onychomycosis. Relapse often occurs when one is reinfected by one's own shoes. This method generally includes heating shoes to temperatures above that which fungi that cause onychomycosis can live. The shoes may be heated using a shoe heater such as a shoe insert attached to a heating element or a specialized heating oven. The shoe heater heats shoes to temperatures above that which fungi that cause Athlete's foot and onychomycosis can survive. Preferably, the shoe heater heats the shoes from a temperature of about 43° C. to about 116° C. In a preferred embodiment, the shoes are heated at a temperature of about 93° C. for about one-half (½) hour. Alternatively, a shoe insert that uses a light-based system adopting Noveon® technology could be used for this device that would emit dual near-infrared wavelengths for 4-15 minutes, optimally 12 minutes. Such a device would eradicate fungus from shoes without exceeding 50° C.

The processes of the present invention, whether used alone or together, result in surprisingly quick and positive results. Currently used remedies can take more than a year to achieve clear looking nails and are prone to relapse. The present invention achieves discernible results immediately, with very good nail appearance, even in severe chronic cases within about 2 months. When nails are lightly infected, the treatment system is most dramatically effective. One treatment can vanquish early manifestations of the disease. The present invention also protects against relapse by creating an unpleasant environment for fungal growth.

When chlorine dioxide is used as a penetration enhancer with terbinafine with the toe sock, nail growth of fungus is controlled within 2 weeks. Other treatments also produce good results as provided by the examples below.

The treatment protocols may be varied and adjusted to the individual. Of particular usage is the application of one treatment for several days to weeks followed by application of a different treatment. This changing of treatments reduces the likelihood of microbial resistance and biofilm protection in the infection. For example changing anti-fungal components appears to help prevent drug resistance or adaptation by the fungus, which can lead to relapse. Additionally, as some powerful treatments cause irritation, particularly with prolonged treatment, interspersing such treatments in a discontinuous but regular (e.g. weekly or biweekly) protocol reduces negative effects while enhancing the effects on the fungus. Between harsh treatments, daily use of milder treatments are used.

Treatments may be as infrequent as once every other day to as often as 6 times per day. Treatment duration is generally between several minutes to all day before washing off the composition. Certain harsh chemical compositions were left on the nails for only 15 minutes while others were not washed off until shortly before another treatment was applied.

Certain components are either too harsh to use frequently, or are only needed occasionally to disrupt the infection or person's tissue. The previous or a new treatment can then be resumed. For example compositions using high concentrations of salicylic acid (about 3 to about 5%) have certain advantages but are used only once every several days or less often. A lesser amount (about 0.5 to about 2%) of salicylic acid may be used on a more daily basis. In another example, treatments 3a and 5a are best only used weekly along with other treatments on the other days such as 1a and 1b.

While some of the data in the experiments below were not double blinded, the placebo effect is unlikely to be a factor since the positive effects occurred very rapidly, much faster than healthy nail could be produced by the body and especially at non-vascularized portions of the nails.

Certain combinations of ingredients have unusual properties. Instead of simply acting in an additive or even a synergistic manner, other effects have been noted. For example, the combination of glycolic acid and benzoyl peroxide has an effect on the skin around the nail to improve its appearance (more pink) and its softness.

While the following examples exemplify the delivery of antifungal and antibiotic agents to the nail, nail bed and surrounding tissues, the present invention is broadly applicable to the delivery of many other biologically active compounds to the surface of the body. Since the penetration enhancing properties have been established for the compounds used in the present invention, the same penetration enhancers may be used to deliver other biologically active compounds also to provide a general pharmaceutical delivery system.

Examples include delivery of a wide selection of pharmaceutical agents to the skin and mucus membranes. Even non-pharmaceutical agents may be so delivered, such as sunscreens and pigments (e.g. melanin) may employ the penetration enhancing agents of the present invention to incorporate them, into the epidermis or if so desired into the living dermal cells.

EXAMPLE 1

In this Example, the outside edges of the infected nails were encased in a hard shelter of fungus-infected skin and keratin debris. Lab results indicated the presence of onychomycosis. The infected nails were first treated by applying heat to the infected nails with far red infrared heat using a heat-generating device having a ceramic heating element to break the fungal seal between skin and nail.

While the nail was still warm from the application of the infrared heat, a narrow, flat plastic device was inserted underneath the nail to first separate the fungus from the underside of the nail. The narrow, flat plastic device was then inserted underneath the nail a second time to separate the fungus from the skin of the toe.

An active chlorine dioxide compound was applied using a dropper to the edges and surface of the infected nails. Generally 2-3 drops were used.

The chlorine dioxide compound was applied again to the infected nails. This time the solution was put into the tips of a latex toe sock in accordance with the present invention. The solution was applied to the skin around the infected nails and over and under the infected nails by putting the latex toe sock on the infected nails.

The sock was worn for about 2 hours. The color of toenails lightened and the cracked, white, fungal-impacted skin was cleared after treatment. As a consequence of treatment, nail fungus was separated from the underside of the nail, as well as from the flesh under the nail with a narrow flat plastic device. This admits oxygen and further topical treatments thus breaking up and collapsing thickened anaerobic fungus. In lightly infected nails, all fungus was easily excised with the narrow, flat plastic device after one treatment.

In heavily infected nails, a tweezers-like narrow cuticle scissor was used to pull out compromised fungus and whitened compromised fungus every few days. Even in cases of heavy fungus, the nail was largely cleared of extreme fungus discoloration within 3 weeks and the appearance of the nail appeared more "normal" to the eye.

When time was a factor, in lieu of the sock treatment, several drops of chlorine dioxide compound were applied directly to the underside of nails and were also applied to saturate the top of the nail. About 2-3 drops were used for each nail.

Several times a day, chlorine dioxide was applied by dropper to saturate the under side of the nail, especially in the evening before bed.

Significant improvement was seen after using the methods of the present invention as described herein. Already heat-compromised fungus was reduced within 24 hours. Yellowing of the nail abated, the nail turned pinker. Hard keratin under the nail softened, fringed and collapsed. The cracked, diseased skin around nails healed.

The invention of this application has been described above both generically and with regard to specific embodiments. Although the invention has been set forth in what is believed to be the preferred embodiments, a wide variety of alternatives known to those of skill in the art can be selected within the generic disclosure. The invention is not otherwise limited, except for the recitation of the claims set forth below.

EXAMPLE 2

An active chlorine dioxide containing composition was applied using a dropper to the edges and surface of the infected nails. The composition had the following components: 2.66% sodium chlorite and citric acid to maintain a pH around 5 was applied by dropper to infected nails.

A 1:1 combination of Terbinafine 1% in gel form and a triple antibiotic was coated under and on top of the nail, covering the nail surface with a thin film.

2.5% Benzoyl peroxide is generously applied to the top and under the nail edge.

Two times a day, the composition was applied by dropper to saturate the under side of the nail, especially in the evening before bed.

Significant improvement was seen after using the methods of the present invention as described herein. Yellowing of the nail was significantly reduced, turning the nail pinker. Hard keratin under the nail softened, fringed and collapsed. The cracked, diseased skin around nails healed.

EXAMPLE 3

This example shows the benefits of using chlorine dioxide as a penetration enhancer. An additional 2% sodium chlorite was added to a 0.66% sodium chlorite formulation of ProFresh® forming chlorine dioxide of about 40 ppm. The solution also contained around 2 ml or 4-6% sodium hypochlorite and citric acid to maintain a pH of around 5. First a dropper was used to wet the surface and underside of the infected nails with active chlorine dioxide (about 40 ppm) in the form of ProFresh®. In this example, it was used double strength, though stronger formulations may be preferable.

Next, terbinafine 1% in gel form was coated under and on top of the nail, covering the nail surface with a white film. The above treatment appears to increase the diffusion of existing topical treatments such as terbinafine through the nail.

The chlorine dioxide compound was applied again to the infected nails. This time the solution was put into the tips of a latex toe sock in accordance with the present invention. The solution was applied to the skin around the infected nails and over and under the infected nails by putting the latex toe sock on the infected nails. The sock was worn for about 2 hours.

For 2-4 times a day, especially at night before going to bed, several drops of chlorine dioxide compound were applied directly to the underside of nails and were also applied to saturate the top of the nail, then a thin layer of terbinafine was added to surface and underside of nail, and active chlorine dioxide was again applied over terbinafine by dropper.

Significant improvement was seen. Fungus was changed to a slightly pasty, flaky consistency that was easily excised with a tweezers like apparatus.

After the first use of active chlorine dioxide, the nail was pinker, and less yellow. Particularly after the use of this invention according to Example 3, fungus that had continued to grow but in a compromised state had deteriorated to a dry but slightly pasty, easily removed substance lacking its former self adhering properties. Onychomycosis was nearly gone.

EXAMPLE 4

Topical applications of various antifungal treatments were applied to fungus infected nails.

TABLE 1A

| BENZOYL PEROXIDE PRODUCTS USED | | | | |
|---|---|---|---|---|
| Invention Product B1 | Invention Product B2 | Invention Product B3 | Invention Product B4 | Invention Product B5 |
| Proactiv Repair Lotion | Clean & Clear | On the Spot | Acne Free | Proactic Advanced Blemish Treatment |
| ACTIVE INGREDIENT | | | | |
| 2.5% Prescription grade benzoyl peroxide | 10% Prescription grade benzoyl peroxide | 2.5% Time release benzoyl peroxide | 10% Time release benzoyl peroxide | Benzoyl peroxide 6% |
| SUSPECTED PENETRATION ENABLER | | | | |
| panthenol, allantoin | allantoin | allantoin | none | Panthenol, Allantoin |
| INACTIVE INGREDIENTS (likely) | | | | |
| Water Ethoxydiglycol Cyclotetrasiloxane propylene glycol cetearyl alcohol dimethicone, glyceryl-stearate PEG-100stearate Cyclopentasiloxane Cyclopentasiloxane panthenol, 2-5% allantoin xanthan gum ceteareth-20 carbomer triethanolamine diazolidinyl urea methylparaben propylparaben | Water Ethoxydiglycol Glycerol Allantoin Tridecyl Stearate Isohexadecane Neopentyl Glycol Dicaprylate/Dicaprate, Tridecyl Trimelitaye Phytosterol Xanthan Gum Propylparaben, Propylene Glycol Methylparaben Diazolindinyl Carbamide | Water Carbomer Disodium EDTA Hydroxypropyl Methylcellulose Laureth-4 Sodium Hydroxide | Water Akyl Benzoate Polysorbate 60 Ethoxydiglycol Glyceryl Stearate Cetearyl Alcohol Glycerin Bisabolol Cetyl Triethylmonium Dimethicone PEG-8 Succinate Tridectl Srearate Isohexadecane Neopentyl Glycol Dicaprylate/Dicaparate Tridecyl Trimelitate Phytosterol Xanthan Gum Tetrasodium EDTA Polylparaben Propylene Glycol Methylparaben Diazolidinyl Carbimide | Water Ethoxydiglycol Cyclopentasiloxane Methylpropanediol Steareth-2 Cyclohexasiloxane Steareth-21 Polyquaternium-37 Propylene glycol Propylene glycol dicaprylate/dicaprate PPG-1 trideceth-6 Panthenol, Diazolidinyl urea Methylparaben Propylparaben Fragrance |

TABLE 1B

Results of Testing Invention Products (I Products)
Containing Benzoyl Peroxide after 3 days.

| Compositions | I Product 1 | I Product 2 | I Product 3 | I Product 4 | I Product 5 |
|---|---|---|---|---|---|
| 1a 3a 3c | 1 | 2 | 2 | 2 | 1 |

Healthy nail appearance was visually observed and ranked in accordance with the below-described standards.
1 - Very good result
2 - No change
3 - Relapse observed Conclusion: B1 and B5 are superior forms of benzoyl peroxide for use according to this method, except when benzoyl peroxide is used with various concentrations of sodium chlorite to create a reaction product, such as chlorine dioxide as in Compositions 6c-6i.

Panthenol and allantoin combined are preferred suspected penetration-enhancing agents for the benzoyl peroxide component of this invention.

TABLE 2A

| Components Defined |
|---|
| Antibiotic |
| Consistent choice of antibiotic is sold as Neosporin. It contains Bacitracin 400 units, Neomycin 3.5 mg, and Polymyxin B 5000 units. Alternatively, oral antibiotics are also acceptable though not preferred. |
| Antifungal Agent |
| A1 2% Miconazole cream in Miconazole 7<br>A2 1% Terbinafine gel in Lamisil AT Gel<br>A3 1% Tolnaflate in Mycocide NS<br>Compositions |
| The chlorine dioxide containing composition is a liquid marketed as Pro Fresh. It can contain from 1-50 ppm Chlorine dioxide as formulated for sale. For purposes of this study, the solution contains about 40 ppm chlorine dioxide. Chlorine dioxide may be a reaction product of 2% sodium chlorite and 5.25% sodium hypochlorite in a citric acid buffer maintaining the pH in the range of 4.5-6.6, preferably around pH 5.<br>Sodium chlorite is 2.67% sodium chlorite or four grams sodium chlorite dissolved in 5 ounces of water. Citric acid is added to maintain a pH range of 4.5-6.6, preferably around pH 5.<br>Glycolic acid is found in a liquid marketed under the name, Proactiv Solution, Revitalizing Toner.<br>17% Salicylic acid is the active ingredient in Wart-Off. It also contains SD Alcohol 40-B, propylene glycol dipelagonate.<br>All other compounds are pure, as described and are mixed with water.<br>Liquid was measured by drops from a standard pipette. A total of 1-3 drops were used atop and under each infected nail.<br>1 Part of a solid is defined as ribbon 0.5 cm wide and 0.5 cm long.<br>At the beginning of treatment of extremely infected nails, double or sometimes triple portions of antifungals, antibiotics and benzoyl peroxide in the ratios listed below may be required to cover rough skin and nails.<br>Subjects washed feet once a day. All treatment regimens were repeated at least twice daily. Compositions remained on infected toes after application until the next application. The two exceptions are 4, where damage to healthy tissue necessitated immediate abandonment of treatment, and 5a where a protocol was consciously chosen that involved 15-minute applications that were rinsed off than followed by Regimen 1a. |

CD - presence of the chlorine dioxide containing composition
SC—sodium chlorite (+ or −0.2%)
AFQ—antifungal quantity
AFT—antifungal type
AB—antibiotic type
BPQ—benzoyl peroxide quantity
BPC—benzoyl peroxide concentration
BPT—benzoyl peroxide type

TABLE 2B

Results of Regimens

| Composition | CD | SC | AFQ | AFT | AB | BPQ | BPC | BPT | Frequency |
|---|---|---|---|---|---|---|---|---|---|
| 1a | x | | 2% | 2 parts | A1/A2* | 1 parts | 2 parts | 2.5% | B1 | 2-3/day |
| 1b | x | | 2% | 2 part | A1/A2* | 1 parts | NONE | | | 2-6/day |
| 1c | x | | 2% | 2 part | A1/A2* | NONE | NONE | | | 2-6/day |
| 2a | x | | | NONE | | NONE | NONE | | | 2-6/day |
| 2b | x | | | 1 part | A1 | NONE | NONE | | | 2-6/day |
| 2c | x | | | 1 part | A2 | NONE | NONE | | | 2-6/day |

TABLE 2B-continued

Results of Regimens

| | Composition | CD | SC | AFQ | AFT | AB | BPQ | BPC | BPT | Frequency |
|---|---|---|---|---|---|---|---|---|---|---|
| 2d | | x | | 1 part | A3 | NONE | NONE | | | 2-6/day |
| 3a | 6% Glycolic | | | 1 part | A2 | 1 part | 1 part | 2.5% | B1 | 1/day |
| 3b | 3% Glycolic | x | 2% | 1 part | A2 | 1 part | 1 part | 2.5% | B1 | 2-3/day |
| 4a | 5% Mandelic | | | 1 part | A1 | 1 part | NONE | | | 2-3 day |
| 4b | 2.5% Mandelic | | | 1 part | A1 | 1 part | NONE | | | 2-3 day |
| 5a | 17% Salicylic | x | 2% | 1 part | A1 | 1 part | NONE | | | 1/day |
| 5b | 17% Salicylic | | | 1 part | A1 | 1 part | NONE | | | 1/day |
| 5c | 4% Salicylic | | | 1 part | A1 | 1 part | NONE | | | 15 min** |
| 5d | 4% Salicylic | | 2.67% | 1 part | A1 | 1 part | NONE | | | 15 min** |
| 5e | 4% Salicylic | | 2.67% | 1 part | A1 | 1 part | 2 parts | 6% | B5 | 15 min** |
| 5f | 4% Salicylic | | 2.67% | 1 part | A1 | 1 part | 2 parts | 6% | B5 | 2/day |
| 5g | 2% Salicylic | | 2.67% | 1 part | A1 | 1 part | 2 parts | 6% | B5 | 2/day |
| 5h | 1% Salicylic | x | 2% | 1 part | A2 | 1 part | 2 parts | 2.5% | B1 | 2/day |
| 6a | | | 8.21% | 1 part | A3 | NONE | | | NONE | 2/day |
| 6b | | | 8.21% | NONE | | NONE | | | NONE | 2-3/day |
| 6c | | | 2.67% | 1 part | A2 | 1 part | 2 parts | 2.5% | B1 | 1/day |
| 6d | | | 2.67% | 1 part | A2 | 1 part | 2 parts | 10% | B2*** | 15 min** |
| 6e | | | 2.67% | 1 part | A1/A2* | 1 part | 2 parts | 10% | B2 | 2/day |
| 6f | | | 2.67% | 1 part | A2 | 1 part | 2 parts | 10% | B4 | 2/day |
| 6g | 6% Glycolic | | 2.67% | 1 part | A1 | 1 part | 2 parts | 10% | B1 | 2/day |
| 6g.1 | 1.25-1.5% Glycolic | | 2.67% | 1 part | A1 | 1 part | 2 parts | 10% | B1 | 2/day |
| 6h | | | 2.67% | 1 part | A2 | 1 part | 2 parts | 6% | B5 | 2/day |
| 6i | | | 1.33% | 1 part | A2 | 1 part | 2 parts | 2.5% | B1 | 2/day |
| 6j | 3% Glycolic | | 1.33% | 1 part | A2 | 1 part | 2 parts | 6% | B5 | 2/day |
| 6k | | | 1.33% | NONE | | NONE | | 6% | B5 | 15 min** |
| 6l | | | 2.67% | NONE | | NONE | | 6% | B5 | 15 min** |
| 6m | | | 1.33% | 1 part | A2 | 1 part | 2 parts | 6% | B1 | 2/day |
| 7 | | | | 1 part | A1 | 1 part | 2 parts | 2.5% | B1 | 2/day |
| 8 | | | | 1 part | A3*** | | | | | 2-3/day |

A1/A2* The primary antifungal used was A2, Miconazole. To counter the adaptive power of the fungus, from one to three times every two weeks, A1, Terbinafine was applied.
15 min** treated 2-3/day and the composition was applied for only fifteen minutes, and then removed. Site was inspected; compromised flakey fungus and dead skin were removed by first wiping with a tissue, then teasing out with a dental pic. Near the nail edges, it was necessary to pluck whitened fungus with cuticle scissors to enhance nail appearance. Then the compositions were reapplied 2 more times for 15 minute durations until all discernible fungus under the nail was gone. Then exemplary daily Regimen 1A was repeated twice daily to maintain nail health.
B2*** There is no discernible difference in results between B2 and B5.
CD = chlorine dioxide used is double strength PROFRESH.
SC = sodium chlorite

TABLE 3

Comparison of Tested Alpha Hydroxy Acids and Chlorine Dioxide in DAILY Regimen Including Antifungal and Antibiotic.

Fungus Quality

1 - Fungus is reduced, is easily removed, nail flattens.
2- Improvement
3 - No Change
4- Relapse. Formerly flakey, easy-to-remove fungus transforms back into a unified, hard, difficult to penetrate plastic-like wall.
Skin Roughness- Reflects compound's effect on fungus impregnated skin around the nails.

1- No Change
2- Slight Skin Roughness Observed
3- 3evere Skin Roughness is Observed
Healthy nail appearance 1-Dramatic improvement
2-Improvement
3-No change
4- Relapse. The white edge of the nail widens. Lateral striations originating at the nail edge begin to intrude on the body of the nail.
Irritation of Skin and Nail 1- Feel nothing
2- Slight pleasant tingle
3- Discomfort Whenever Stage 4 occurs, or an irritation level 3 is reached, testing of listed Composition was abandoned.

TABLE 3A

After One - Three Days

| | Fungus Quality | Skin Roughness | Nail Appearance | Irritation |
|---|---|---|---|---|
| 1A | 2 | 2 | 1-2 | 1 |
| 1b | 3 | 2 | 2 | 1 |
| 1c | 3 | 2 | 2 | 1 |
| 2a | 3 | 2 | 2 | 0 |
| 2b | 2-3 | 2 | 2 | 0 |
| 2c | 2-3 | 2-1 | 1 | 0 |
| 2d | 3 | 2 | 2 | 0 |
| 3a | 1 | 1 | 1 | 0-1 |
| 3b | 1 | 1 | 2 | 0-1 |
| 3c | 1 | 1 | 2 | 0-1 |
| 4a | 2 | 2 | 2 | 2 |
| 4b | 2 | 2 | 2 | 0 |
| 5a | 3 | 3 | 4 | 2 |
| 5b | 1-2 | 3 | 1-2 | 1-2 |
| 5c | 2-3 | 2-3 | 1-2 | 0 |
| 5d | 1-2 | 2-3 | 3 | 1-2 |
| 5e | 1-2 | 2-3 | 1 | 1-2 |
| 5f | 1 | 2 | 1 | 1-2 |
| 5g | 1 | 2 | 1 | 1 |
| 5h | 1 | 1-2 | 1 | 1 |
| 6a | 2-3 | 3 | 2-3 | 2 |
| 6b | 2-3 | 3 | 3-2 | 2 |
| 6c | 1-2 | 2 | 3 | 2 |
| 6d | 1 | 1 | 1-2 | 1 |
| 6e | 1 | 1 | 1-2 | 1 |
| 6f | 1 | 1 | 3 | 1 |
| 6g | 1 | 1 | 1 | 1- |
| 6g.1 | 1 | 1 | 1 | 1 |
| 6h | 1 | 1 | 1-2 | 1 |

TABLE 3A-continued

After One - Three Days

| | Fungus Quality | Skin Roughness | Nail Appearance | Irritation |
|---|---|---|---|---|
| 6i | 1 | 1 | 1-2 | 1 |
| 6j | 2-1 | 1 | 1-2 | 1 |
| 6k | 1 | 1 | 1-2 | 0 |
| 6l. | 1 | 1 | 1 | 0 |
| 6m | 1 | 1 | 1 | 1 |
| 7 | 3-2 | 3 | 3-2 | 0 |
| 8 | 3 | 2 | 3 | 0 |

TABLE 3B

After Seven Days

| | Fungus Quality | Skin Roughness | Nail Appearance | Irritation |
|---|---|---|---|---|
| 1A | 1 | 1-2 | 1-2 | 1 |
| 1b | 2-1 | 2-1 | 1-2 | 1 |
| 1c | 2-1 | 2-1 | 2 | 1 |
| 2a | 2 | 2 | 1-2 | 0 |
| 2b | 2 | 2 | 1-2 | 0 |
| 2c | 2-1 | 2 | 1-2 | 0 |
| 2d | 2 | 2 | 2 | 0 |
| 3a | 3 | 1 | 4 | 0 |
| 3b | 3 | 1 | 3-4 | 0-1 |
| 3c | 3 | 1 | 4 | 0-1 |
| 4a | Discontinued, see irritation | | 4 | 2 |
| 4b | 4 | 2 | 4 | 0 |
| 5a | Discontinued, see irritation, relapse | | | 2 |
| 5b | 2 | 3 | 2-1 | 0 |
| 5c | | | | |
| 5d | | | | |
| 5e | | | | |
| 5f | | | | |
| 5g | | | | |
| 5h | | | | |
| 6a | 2-3 | 3 | 2-3 | 2 |
| 6b | 4-3 | 3 | 3-2 | 2 |
| 6c | Discontinued, see irritation | | | 2 |
| 6d | 1 | 1 | 1-2 | 1 |
| 6e | 1 | 1 | 1-2 | 1 |
| 6f | Discontinued, ineffective | 1 | 3 | 1 |
| 6g | 1 | 1 | 1 | 1- |
| 6g.1 | | | | |
| 6h | 1 | 1 | 1-2 | 1 |
| 6i | 1 | 1 | 1-2 | 1 |

TABLE 3B-continued

After Seven Days

| | Fungus Quality | Skin Roughness | Nail Appearance | Irritation |
|---|---|---|---|---|
| 6j | 2-1 | 1 | 1 | 1 |
| 6k | | | | |
| 6l. | | | | |
| 6m. | 1 | 1 | 1 | 0-1 |
| 7 | 3-2 | 3 | 3-2 | 0-1 |
| 8 | 3 | 2 | 3 | 0 |

TABLE 3C

After 30+ Days

| | Fungus Quality | Skin Roughness | Nail Appearance | Irritation |
|---|---|---|---|---|
| 1A | 1 | 1-2 | 1-2 | 1 |
| 1b | 2-1 | 2-1 | 3-4 | 1 |
| 1c | 2-1 | 2-1 | 4 | 1 |
| 2a | 2 | 2 | 4 | 0 |
| 2b | 2 | 2 | 4 | 0 |
| 2c | 2-1 | 2 | 4 | 0 |
| 2d | 2 | 2 | 4 | 0 |
| 3a | 3 | 1 | 4 | 0 |
| 3b | 3 | 1 | 4 | 0-1 |
| 3c | 3 | 1 | 4 | 0-1 |
| 4 | 4 | 2 | 4 | 0 |
| 5a | Discontinued, see irritation, relapse | | | 2 |
| 5b | 2 | 3 | 2-1 | 1 |
| 5c | | | | |
| 5d | | | | |
| 5e | | | | |
| 5f | | | | |
| 5g | | | | |
| 5h | | | | |
| 6a | 2-3 | 3 | 4 | 2 |
| 6b | 4-3 | 3 | 4 | 2 |
| 6c | Discontinued, see irritation | | | 2 |
| 6d | 1 | 1 | 1-2 | 1 |
| 6e | 1 | 1 | 1-2 | 1 |
| 6f | Discontinued, ineffective | 1 | 3 | 1 |
| 6g | | | | |
| 6g.1 | | | | |
| 6h | 1 | 1 | 1-2 | 1 |
| 6i | 1 | 1 | 1-2 | 1 |
| 6j | | | | |
| 6k | | | | |
| 6l. | | | | |
| 6m. | | | | |
| 7 | Discontinued, fungal skin unaffected/rough skin. | | | 0-1 |
| 8 | 3 | 2 | 4 | 0 |

TABLE 4

Describing Effects of Tested Compounds

| Fungus under nail | Color of Nail | Quantity of Fungus | Relapse |
|---|---|---|---|
| 1a. Chlorine dioxide/chlorite salts 2% w/ antibiotic and antifungal Miconazole and Benzoyl Peroxide 2.5 | | | |
| Flakey, easily removed | white edge, pink body | Reduced | No |
| 1b. Chlorine dioxide/chlorite salts 2% w/ antibiotic and antifungal Miconazole and Benzoyl Peroxide 2.5 | | | |
| Flakey, easily removed | white edge, pink body | Reduced | No |
| 1c. Chlorine dioxide/chlorite salts 2% w antibiotic and antifungal Miconazole 2% | | | |
| Flakey, Easily removed | Yellow edge | Reduced | Minor |

TABLE 4-continued

| | | | |
|---|---|---|---|
| 2a. Chlorine dioxide | | | |
| Flakey, can be removed | initially good, yellow edge<br>Edge: lateral thickening, striations | Reduced | Yes |
| 2b. Chlorine dioxide/1% Tolnaflate | | | |
| Flakey, can be removed | initially good, yellow edge<br>Edge: lateral thickening, striations | Reduced | Yes |
| 2c. Chlorine dioxide/1% Terbinafine gel | | | |
| Flakey, can be removed | initially good, yellow edge<br>Edge: lateral thickening, striations | Reduced | Yes |
| Flakey, can be removed | yellow edge, lateral thickening<br>Edge: lateral thickening, striations | Reduced | Yes |
| 3a. Glycolic Acid 5% w/antibiotic and antifungal Miconazole 2% and Benzoyl Peroxide | | | |
| Flakey, can be removed<br>as Keratolytic<br>*only used discontinuously | Nail edge white; body pink | reduced | N/A* |
| 3b Glycolic Acid 2.5% w/chlorine dioxide/chlorite salts + antibiotic and antifungal Miconazole 2% + Benzoyl Peroxide | | | |
| Flakey, can be removed | White of nail diffuses,<br>Thickens, Widens laterally | Increased after 1 week | Yes |
| 3c Glycolic Acid 2.5% interspersed w/5% every 2-3 days w/antibiotic and antifungal Miconazole 2% and Benzoyl Peroxide | | | |
| Flakey, can be removed | White of nail diffuses,<br>Widens laterally | Increased after 1 week | Yes |
| 4a. 5% Mandelic Acid w/ chlorine dioxide/chlorite salts + antibiotic and antifungal Miconazole 2% | | | |
| Hard to remove<br>*Use discontinued because of pain | Yellow edge, Body:<br>Brown tone | Increased | N/A* |
| 4b. 2.5% Mandelic Acid w/ chlorine dioxide/chlorite salts + antibiotic and antifungal Miconazole 2% | | | |
| Hard to remove | Yellow edge, Body: Brown tone | Increased | Yes |
| 5a. 17% Salicylic Acid w/ chlorine dioxide/chlorite salts + antibiotic and antifungal Miconazole 2% | | | |
| Lateral increase within hours | Thick edge/striations<br>Skin around nails roughened | Increased | Yes |
| 5b. 17% Salicylic Acid + antibiotic and antifungal Miconazole 2% | | | |
| Flakey, easily removed<br>*only used discontinuously as Keratolytic | slight yellow edge. good<br>Skin around nails roughened | Reduced | N/A* |
| 5c. 4% Salicylic Acid + antibiotic and antifungal Miconazole 2% | | | |
| Good separation between nail &<br>fungus. Fungus not easily removed. | white edge | little change | insufficient data |
| 5d. 4% Salicylic Acid w/ 2.67% chlorine dioxide/chlorite salts + antibiotic and antifungal Miconazole 2% | | | |
| Good separation between nail &<br>fungus. Fungus removable.<br>Fungus dry, scaly | blurred, yellow edge | fungus reduced | insufficient data |
| 5e. 4% Salicylic Acid w/ 2.67% chlorine dioxide/chlorite salts w/ 6% benzoyl peroxide + antibiotic and antifungal Miconazole 2% | | | |
| Good separation between nail &<br>Fungus. Fungus removable<br>Fungus dry, scaly | white defined edge<br>after dead fungus is cleared | fungus reduced<br>significantly | insufficient data |
| 5f. 4% Salicylic Acid w/ 2.67% chlorine dioxide/chlorite salts w/ 6% benzoyl peroxide + antibiotic and antifungal Miconazole 2% | | | |
| Good separation between nail &<br>Fungus. Fungus removable<br>significantly easily the next day.<br>Fungus dry, scaly | white defined edge | fungus reduced | insufficient data |
| 5g. 2% Salicylic Acid w/ 2.67% chlorine dioxide/chlorite salts w/ 6% benzoyl peroxide + antibiotic and antifungal Miconazole 2% | | | |
| Good separation between nail &<br>Fungus. Fungus dry, scaly; is easily<br>Significantly removable the next day. | white defined edge | fungus reduced | insufficient data |

TABLE 4-continued

5h. 1% Salicylic Acid w/ chlorine dioxide and 2% chlorite salts w/ 2.5% benzoyl peroxide + antibiotic and antifungal Terbinafine 2%

| | | | |
|---|---|---|---|
| Good separation between nail & Fungus. Fungus dry, scaly; is easily Significantly removable the next day. | white defined edge | fungus reduced significantly | insufficient data |

6a. 8.21% Sodium Chlorite w/ Tolnaflate 1%

| | | | |
|---|---|---|---|
| Fungus turns orange and Crystalline. Can be removed; not easily, Painful | Nail is orange toned Unattractive | Fungus is moderately reduced | yes |

6b. 8.21% Sodium Chlorite

| | | | |
|---|---|---|---|
| Fungus turns orange and Can be removed; not easily Painful. Fungal skin around nail is crusty, slightly orange in color | Nail is orange toned Unattractive | Fungus is moderately reduced | yes |

6c. 2.67 Sodium Chlorite reacts w/ 2.5% Benzoyl Peroxide + antifungal + antibiotic

| | | | |
|---|---|---|---|
| Easily Removed Painful | good edge, then relapse | inconclusive | Mild |

6d. 2.67% Sodium Chlorite + 10% Benzoyl Peroxide to create Chlorine dioxide + antifungal + antibiotic

| | | | |
|---|---|---|---|
| Easily Removed Applied for 15 minutes, and then removed. Repeated 3 x until all fungus is removed from under nail. | White edge, transparent | Reduced significantly | No |

6e. 2.67% Sodium Chlorite + 10% Benzoyl Peroxide to create Chlorine dioxide w/antifungal + antibiotic

| | | | |
|---|---|---|---|
| Easily Removed | White edge, transparent | Reduced significantly | No |

6f. 2.67% Sodium Chlorite + 10% time release Benzoyl Peroxide to create Chlorine dioxide w/Terbinafine + antibiotic

| | | | |
|---|---|---|---|
| Can be removed | lateral widening nail edge | no change | minor |

6g. 2.67% Sodium Chlorite + 2.5% Glycolic acid w/ 10% Benzoyl Peroxide w/antifungal + antibiotic

| | | | |
|---|---|---|---|
| Easily removed | very white edge, body pink/transparent | inconclusive | No |

6g.1. 2.67% Sodium Chlorite + 1% Glycolic acid w/ 6% Benzoyl Peroxide w/antifungal + antibiotic

| | | | |
|---|---|---|---|
| Easily Removed | very white edge, body pink/transparent | no discernable change | No |

6h. 2.67% Sodium Chlorite + 6% Benzoyl Peroxide to create Chlorine dioxide w/antifungal + antibiotic

| | | | |
|---|---|---|---|
| Easily removed | Cleanly defined edge | Reduced significantly | minor |

6i. 1.33% Sodium Chlorite + 2.5% Benzoyl Peroxide to create Chlorine dioxide w/antifungal + antibiotic

| | | | |
|---|---|---|---|
| Easily removed | slight lateral striation | Reduced | inconclusive |

6j. 1.33% Sodium Chlorite + 2.5% Glycolic acid w/ 10% Benzoyl Peroxide w/antifungal + antibiotic

| | | | |
|---|---|---|---|
| Easily removed Appears softer | very white edge, body pink/transparent white of nail has softer edge with less defined edges. | inconclusive | Not to date |

6k 1.33% Sodium Chlorite and 6% Benzoyl Peroxide. NO antifungal. NO antibiotic for 15 minutes

| | | | |
|---|---|---|---|
| Very Easily Removed | white edge, body pink/transparent | Reduced | Not to date |

6l 2.66% Sodium Chlorite 6% Benzoyl Peroxide. NO antifungal. NO antibiotic

| | | | |
|---|---|---|---|
| Very easily Removed Came out in strips | white edge, body pink/transparent one nail has slight yellow tint on edge | Reduced significantly | Not to date |

6m. 1.33% Sodium Chlorite reacts w/ 6% Benzoyl Peroxide to create Chlorine dioxide w/antifungal + antibiotic

| | | | |
|---|---|---|---|
| Easily removed | good | Reduced | Not to date |

TABLE 4-continued

| 7. 2.5% Benzoyl Peroxide with antibiotic and antifungal Miconazole 2% | | | |
|---|---|---|---|
| Adheres to itself. Difficult to remove | Discoloration reduced entire nail appears white | inconclusive | N/A* |
| Treatment abandoned because after 2-3 weeks, entire nail began to turn white* | | | |
| Fungal skin around nail remains crusted, is largely unaffected by treatment. | | | |

| 8. 1% Tolnaflate | | | |
|---|---|---|---|
| No appreciable change | No Change | No Change | N/A |

TABLE 5

| | TREATMENTS USED | | |
|---|---|---|---|
| | Subject A | Subject B | Subject C |
| 1a | x | x | |
| 1b | x | x | |
| 1c | x | | |
| 1d | x | | |
| 2a | x | | |
| 2b | x | | |
| 2c | x | | |
| 2d | x | | |
| 3a | x | x | |
| 3b | x | | |
| 3c | x | | |
| 4 | x | | |
| 5a | x | | |
| 5b | x | | |
| 5c | x | | |
| 5d | x | | |
| 5e | x | | |
| 5f | x | | |
| 5g | x | | |
| 6a | x | | |
| 6b | x | | |
| 6c | x | x | |
| 6d | x | | x |
| 6e | x | x | x |
| 6f | x | | |
| 6g | x | | |
| 6g.1 | x | | |
| 6h | x | | |
| 6i | x | x | |
| 6j | x | | |
| 7 | | x | |
| 8 | x | | |

Previous to this study, Subject A had used ReClear A/F with barely discernible results that led to relapse, Nonyx Gel, with no result, Tonaflate and Fungi Clear with no result. The subject was also treated with Sporonox, and Gris-Peg, 250 mg without positive results. Her toe fungus infection dates back to 1995 when she was first diagnosed. All her toes were infected at the time of this study.

Subject B had used assorted topical creams, and then gave up attempts at treatment before this study. He is 66 years old and has been diagnosed with onychomycosois. He has had 9 fungal toes for six years.

Subject C has never attempted to treat his toe fungus infection, which began in 1944. He is 86 years old.

All subjects treated with the preferred embodiments of this invention responded positively to treatment. Though nine of his toes were infected, subject B's Right toe 1 and Left toe 1 were extremely distorted and discolored by Onychomycosis at the time of this study. Subject C was treated with the Regimen detailed in 6e. The diseased nail came off within 24 hours after treatment revealing another layer of fungus. About 60% of that fungus was removed after 2 more 15 minute treatments according to 6e, and two treatments according to 6d spaced two days apart.

Subject B showed positive results within three days/and 6 treatments of composition 1a on toes 1-5 of his left foot. He also responded positively when treated according to 1b on left toes 3 and 4 according to the present invention.

Two toes of Subject B (Left 1 and 2) were treated according to Composition 7. That regimen was abandoned because the fungus impacted skin around the nails, remained crusted and appears unaffected by treatment. Also the fungus appeared to maintain its wall—like nature and was difficult to remove when compared to preferred regimens.

Subject A has nearly clear toes after treatment according to this invention.

EXAMPLE 5

Test on Toenail Sample

Subject C's left "big" toenail completely detached from his left foot after two treatments according to treatment with composition 6e followed by 1 evening and morning treatment according to Regimen 6c. It was somewhat loose before treatment, apparently held to the foot by the fungus that was dissolved by the treatments. A layer of fungus still adhered to the upper third of the nail.

Thin strands of tape were applied to the nail to divide the front of the nail into quadrants. The following compositions were applied to the surface of the 4 quadrants of the detached nail according to the chart below.

| | Quadrant number | | | |
|---|---|---|---|---|
| | 1 | 2 | 3 | 4 |
| Treatment composition | 6k | 6m | 6l | 6g |

A clear separation was made between the quadrants. The compositions were applied only to the surface of the nail, not allowing the compositions to contact the back of the nail. A slightly damp paper towel was placed beneath the nail. Plastic wrap was positioned under the paper towel and nail and also surrounded all with plastic wrap, taking care to leave the front of the nail exposed to air. The plastic was taped down to create an oxygen-depleted environment. The nail was left in the sun outside on an 86-degree day for 45 minutes.

After treatment, the nail was removed, flipped over and, a pointed dental pic applied to the 4 quadrants. There was a release of fungus in all four quadrants. However, there was a clear 4 step level of success.

Treatment composition 6g, quadrant 4 is clearly superior. All the fungus in that quadrant came up from the nail in a strip, stopping at the line of division created by the tape on the obverse side. Treatment composition 6m, quadrant 2 was the next most effective. The fungus came up in patches from that quadrant. Treatment compositions 6L and 6k were also somewhat effective. Fungus came up in patches on the 6L quadrant, with clear places on the nail achieved after minor effort with the dental pic. Fungus could be removed from 6K with slightly more difficulty. The success achieved entailed removing layers of fungus instead of strips. Some clear patches were achieved. Twenty-four hours after treatment, almost all dark striations of discoloration are gone, even in places where the fungus still adheres to the back, except for a narrow area near the lateral line of division between quadrants on the on the side of the nail where antifungal and antibiotic were not applied.

Since the treatments removed fungus except for the portions masked by tape, it is concluded that the treatments are capable of penetrating the nail from the top of the nail to the underside.

EXAMPLE 6

Treatment was performed as above using the chlorine dioxide (about 40 ppm) with added 2% sodium chlorite, 5.25% sodium hypochlorite and citric acid to maintain a pH around 5 was mixed and stored in an impermeable plastic container. In a separate container 6% glycolic acid was prepared. Both were applied by dropper to the top and under side of the edge of the infected nail. The order of addition was glycolic acid first, then antifungal, then antibiotic, then the chlorine dioxide containing solution.

Then a layer of antifungal B mixed with a topical antibiotic is applied to top and under the edge of the infected nail as above and 1 part antifungal: 1 part topical antibiotic cream rubbed onto the top of the nail and nail bed. 2-3 parts 2.5% benzoyl peroxide was loosely applied over the antifungal/antibiotic coating and under the edge of the infected nail.

The combination was left on the nails for as short a period as 10 minutes to 24+ hours. Ideally, the product stays on the nail for a day or evening until the next treatment.

A ten or fifteen minute treatment is enhanced by the use of a toe sock. In that case, one extra part benzoyl peroxide and 3-5 more drops of the chlorite salt solution is placed in the toe sock and placed on the infected toe.

This procedure is recommended as an exfoliating step repeated at least once a week, but no more than 7 times a week to speed removal of dead or compromised fungus and debris. After this step, weakened fungus is removed from under the nail with a pincer like cuticle scissor, or flat plastic tool.

Nail health is maintained and fungus is further reduced by at least twice daily treatments as above but with treatment compositions 1A or 6E or 6H.

The invention of this application has been described above both generically and with regard to specific embodiments. Although the invention has been set forth in what is believed to be the preferred embodiments, a wide variety of alternatives known to those of skill in the art can be selected within the generic disclosure. The invention is not otherwise limited, except for the recitation of the claims set forth below.

What is claimed is:

1. A method for treating or preventing a fungal infection of nail or skin, comprising: applying one or more compositions to a surface of the infection or nearby tissue; wherein said compositions comprise a specific antifungal agent and a metal chlorite salt, and wherein the resultant composition contains less than 1 ppm chlorine dioxide and is not applied to an oral cavity.

2. The method of claim 1 wherein said compositions further comprise an alpha hydroxy acid.

3. The method of claim 1, further comprises a broad spectrum antibiotic agent.

4. The method of claim 1, wherein the metal chlorite salt comprises at least 1% by weight.

5. The method of claim 4, wherein the metal chlorite salt comprises at least 2% by weight.

6. The method of claim 1, wherein the specific antifungal agent is selected from the group consisting of; amorolfine, amphotericin B, carbol-fuchsin, ciclopirox, clotrimazole, dapsone econazole, fluconazole, flucytosine, griseofulvin, Gentian Violet, haloprogin, itraconazole, ketoconazole, mafenide, miconazole, naftifine, nystatin, oxiconazole, silver sulfadiazine, sulconazole terbinafine, tioconazole, tolnafiat, undecylenic acid, voriconazole, and pharmaceutically acceptable salts and esters thereof.

7. The method of claim 1 wherein the surface is a nail.

8. A method for treating or preventing nail fungus, comprising applying a first composition for treating or preventing nail fungus, but not a second composition for treating or preventing nail fungus, to at least one nail exposed to or infected with nail fungus multiple times over a period of at least three days followed by applying said second composition for treating or preventing nail fungus, but not said first composition, for treating or preventing nail fungus, wherein said first composition and said second composition differ in their chemical components, wherein the first composition comprises a metal chlorite salt and contains less than 1 ppm chlorine dioxide, and wherein the nail fungus has not relapsed during the treatment.

9. The method of claim 8, further comprising at least one subsequent application with said first composition, but not the second composition, within 3-10 days of applying said second composition, but not the first composition, wherein the nail fungus has not relapsed during the treatment.

10. The method of claim 8, wherein said first composition and said second composition contain different specific antifungal agents.

11. The method of claim 8, wherein said first composition and said second composition differ in the type or amount of organic acids in each composition.

12. The method of claim 10, wherein the specific antifungal agent is selected from the group consisting of; amorolfine, amphotericin B, carbol-fuchsin, ciclopirox, clotrimazole, dapsone econazole, fluconazole, flucytosine, griseofulvin, Gentian Violet, haloprogin, itraconazole, ketoconazole, mafenide, miconazole, naftifine, nystatin, oxiconazole, silver sulfadiazine, sulconazole terbinafine, tioconazole, tolnafiat, undecylenic acid, voriconazole, and pharmaceutically acceptable salts and esters thereof.

13. A method for delivering a bioactive compound to a nail surface or a surface of a body comprising; adding the bioactive compound and a penetration enhancer containing composition sequentially or simultaneously to the nail surface or the surface of the body to form a further composition, wherein penetration through the nail or the surface of the body of the bioactive compound is enhanced by the penetration enhancer, wherein the penetration enhancer is a metal chlorite salt, and wherein the further composition contains less than 1 ppm chlorine dioxide and is not applied to an oral cavity.

14. The method of claim 13, wherein the bioactive compound is a specific antifungal drug or a broad spectrum antibiotic agent.

15. The method of claim 14 wherein the specific antifungal drug is selected from the group consisting of; amorolfine, amphotericin B, carbol-fuchsin, ciclopirox, clotrimazole, dapsone econazole, fluconazole, flucytosine, griseofulvin, Gentian Violet, haloprogin, itraconazole, ketoconazole, mafenide, miconazole, naftifine, nystatin, oxiconazole, silver sulfadiazine, sulconazole terbinafine, tioconazole, tolnafiat, undecylenic acid, voriconazole, and pharmaceutically acceptable salts and esters thereof.

* * * * *